United States Patent [19]

Bradley et al.

[11] 4,233,991
[45] Nov. 18, 1980

[54] URETHRAL CATHETER PULLER

[75] Inventors: William E. Bradley; William M. Klatt, both of Minneapolis; Charles C. Kuyava, Brooklyn Center; Robert D. Dreher, Roseville, all of Minn.

[73] Assignee: American Medical Systems, Inc., St. Louis Park, Minn.

[21] Appl. No.: 970,465

[22] Filed: Dec. 18, 1978

Related U.S. Application Data

[63] Continuation-in-part of Ser. No. 696,318, Jun. 15, 1976, Pat. No. 4,199,916.

[51] Int. Cl.³ ............................................. A61B 5/10
[52] U.S. Cl. ................................... 128/733; 128/748; 128/349 R
[58] Field of Search ............... 128/642, 733, 748, 772, 128/780, 349 R, 348, DIG. 9

[56] References Cited

U.S. PATENT DOCUMENTS

| | | | |
|---|---|---|---|
| 4,066,071 | 1/1978 | Nagel | 128/DIG. 9 |
| 4,073,287 | 2/1978 | Bradley et al. | 128/642 |

OTHER PUBLICATIONS

Ghoneim et al., "Urethral Pressure Profile", Urology May 1975, vol. 5, No. 5, pp. 632-637.
Harvard Apparatus Co., Inc., Bulletin Jun. 1965, pp. 2-8.
Edwards et al., "The Urethral Pressure Profile: Application", B.J. Urology (1974), 46, 325-326.
Andersen et al., "Electromyographic and Gas Urethral Pressure Profile", Urology, May 1976, vol. 7, No. 5, pp. 561-565.

*Primary Examiner*—Lee S. Cohen
*Attorney, Agent, or Firm*—Williamson, Bains, Moore & Hansen

[57] ABSTRACT

The urethral catheter puller described in this application provides a convenient apparatus for performing urological diagnostic procedures such as urethral pressure profilometry and urethral electromyographic profilometry. In practice, a urethral catheter is mounted on catheter supports attached to the boom of the puller. The boom is equipped with positioning apparatus so that the catheter supports may be positioned in close proximity to the patient. The puller allows the catheter to be pulled in a horizontal or vertical direction, thus allowing the patient to stand or lie in a bed during the diagnostic procedure. The catheter supports are equipped with suitable structures to control the motion of the catheter as it is withdrawn from the urethra of the patient. A variable speed drive is provided to control the rate at which the catheter is withdrawn.

8 Claims, 12 Drawing Figures

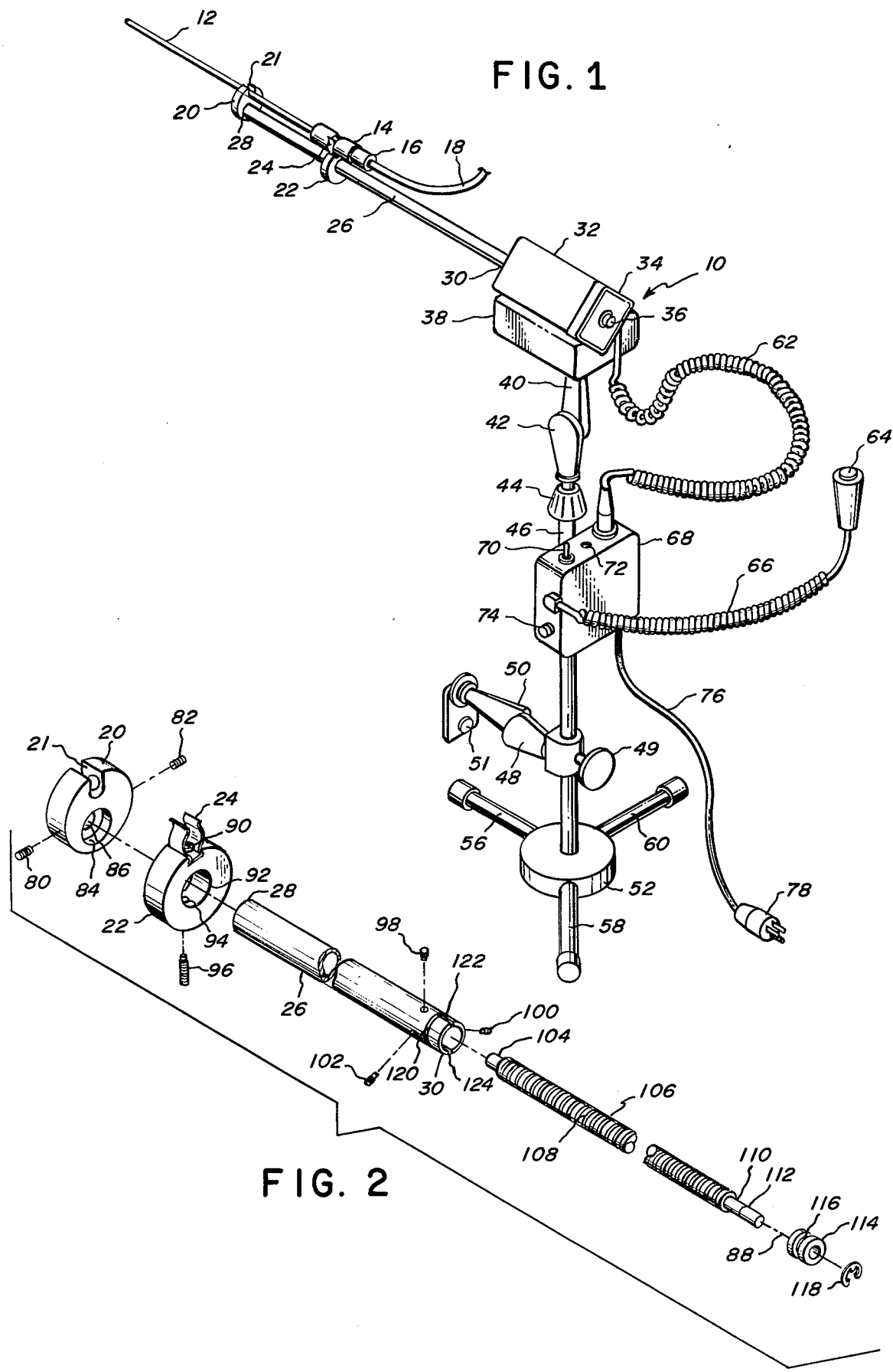

4,233,991

URETHRAL CATHETER PULLER

BACKGROUND OF THE INVENTION

This application is a continuation-in-part of application Ser. No. 696,318 filed June 15, 1976, now U.S. Pat. No. 4,199,916.

This invention relates generally to medical diagnostic instrumentation and relates more particularly to mechanical structures for controlling the withdrawal of a catheter from a urethra.

Profilometry, the urinary diagnostic technique most relevant to the instant invention, involves the generation of a urethral pressure profile or a urethral electromyographic profile. The urethral pressure profile is a graphical record of pressure within the urethra at successive points along its length. The urethral electromyographic profile is a graphical record of the electrical activity of muscles surrounding the urethra at successive points along the urethral length. The purpose of profilometry procedures is to investigate and test the behavior of the complex urinary tract. One of the uses for profilometry is the diagnosis of symptoms associated with urinary incontinence.

A prior art mechanical device for withdrawing a urethral catheter at a constant rate for recording a urethral pressure profile was described by Ghoneim et al in "Urethral Pressure Profile" in *Urology*, May 1975, pages 632 to 637. Ghoneim et al described a catheter puller which consists of a traveler which moves forward or backward over a motor driven endless screw. The puller also included an electronic switch which controlled the speed and direction of displacement of the motor. A hollow plexiglass tube was fixed to the end of the traveler support to prevent kinking of the urethral catheter.

SUMMARY OF THE INVENTION

The instant invention comprises a urethral catheter puller which may be used in a urological profilometry procedure to withdraw a catheter from a patient's body at a controlled rate.

Thus a primary object of this invention is to provide an apparatus for withdrawing a urethral catheter from a patient's body at a controlled rate.

Another object of this invention is to provide a urethral catheter puller usable in profilometry procedures when the patient is either standing, seated or supine. It is desirable that a puller be capable of operating satisfactorily in many different patient-test situations.

An object of this invention is to provide a urethral catheter puller in which parts likely to come in contact with a patient may be sterilized.

A further object of this invention is to provide a urethral catheter puller in which the motion of the catheter is reliabily controlled and the catheter is prevented from kinking or drooping.

Another object of this invention is to provide a urethral catheter puller having catheter supports into which a urethral catheter may be easily and rapidly mounted.

A further object of this invention is to provide a urethral catheter puller having catheter supports which may be positioned in close proximity to the point of exit of a urethral catheter from a patient's body.

Another object of this invention is to provide a urethral catheter puller having a movable catheter support which is driven by a motor for catheter withdrawal and which may be manually repositioned after a profilometry procedure has been completed.

A still further object of this invention is to provide a drive means for a urethral catheter puller which accurately controls the rate at which a urethral catheter is withdrawn from a patient's body.

Yet another object of this invention is to provide a urethral catheter puller controlled by a push button hand switch so that the catheter will not be pulled unless the hand switch is held down.

These and other objects of this invention, along with features of novelty appurtenant thereto, will appear or become apparent in the course of the following description.

BRIEF DESCRIPTION OF THE DRAWINGS

In the following drawings, which form a part of the specification and are to be construed in conjunction therewith, and in which like reference numerals have been employed to indicate like parts in the various views:

FIG. 1 is a perspective view of the urethral catheter puller apparatus showing a urethral catheter mounted thereon;

FIG. 2 is an exploded perspective view of a portion of the apparatus of FIG. 1 showing structures mounted in or on the boom;

DETAILED DESCRIPTION OF THE DRAWINGS

Figure 3:
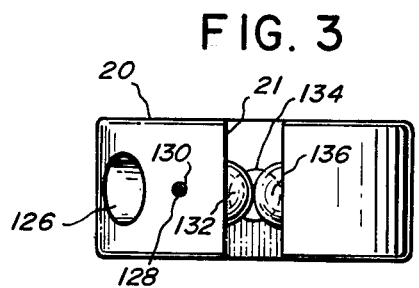
FIG. 3 is a top view of the forward catheter support shown in FIG. 1.

Referring first to FIG. 1, the urethral catheter puller is denoted generally by the reference numeral 10. A urethral catheter 12 having a catheter connector 14, tubing connector 16, and tubing 18 is shown mounted on the puller 10. Catheter 12 is inserted in slot 21 of forward catheter support 20. Catheter connector 14 is inserted in catheter clip 24 which is mounted on rearward catheter support 22. Forward catheter support 20 is firmly attached to forward boom end 28 of boom 26. Rearward catheter support 22 is slidably mounted on boom 26.

Rearward boom end 30 is insertably mounted in drive box 32. Speed control knob 36 is mounted on drive box cover 34, which in turn is mounted on drive box 32. Drive box 32 is supported by drive box support 38. Drive box support 38 is removably connected to pivoting arm 40. Arm 40 is pivotably connected to arm 42, thus allowing boom 26 to assume a plurality of angular orientations. Arm 42 is capable of moving vertically and rotating about the axis of post 46. Adjustment knob 44 connects arm 42 with post 46 and locks arm 42 in place when tightened. Post 46 is supported by stand 52 and is stabilized by legs 56, 58 and 60 which rest on the ground.

Arm 48 is slidably mounted on post 46 and may be locked in a plurality of vertical positions by tightening adjustment knob 49. Pivoting arm 50 is pivotably attached to arm 48. Drive box support 38 is capable of being attached to pivoting arm 50 by means of mounting screw 51. When the catheter 12 is to be pulled vertically as from a standing patient, drive box 38 is normally attached to pivoting arm 50. When catheter 12 is to be pulled horizontally as from a bedridden patient, drive box support 38 is normally attached to pivoting arm 40. Drive box support 38 need not be attached to either arm 40 or arm 50 but may be placed on a table or on a bed.

Electronic cable 62 connects drive box 32 with electronics box 68. Power switch 70, pilot light 72, and fuse 74 are mounted on electronics box 68. Switch cable 66 connects motor control switch 64 to electronics box 68. Power cable 76 connects electronics box 68 with an external source of power through power plug 78.

In operation, catheter 12 is mounted in forward catheter support 20 and rearward catheter support 22 when rearward catheter support 22 is located near forward boom end 28. When a profilometry test is to be made, motor control switch 64 is depressed causing rearward catheter support 22 to slide along boom 26 towards rearward boom end 30. A slight amount of tension is produced in catheter 12 between forward catheter support 20 and rearward catheter support 22 to prevent catheter 12 from kinking or drooping. The rate at which rearward catheter support 22 slides along boom 26 is controlled by adjusting speed control knob 36.

Referring now to FIG. 2, forward end 28 of boom 26 slidably inserts in bore 84 of forward catheter support 20 and is secured in place by mounting screws 80 and 82. Rearward catheter support 22 is equipped with a bore 92 allowing rearward catheter support 22 to slide upon boom 26. Catheter clip 24 is secured to rearward catheter support 22 by means of mounting screw 90. Leadscrew follower 96 is threadably inserted in bore 94 of rearward catheter support 22.

Leadscrew 106 having threads 108 is mounted inside boom 26. Leadscrew forward end 104 is journaled in bore 86 of forward catheter support 20. Leadscrew rearward end 110 is journaled in sleeve bearing 114. Bearing 114 is maintained in place on leadscrew rearward end 110 by means of retainer clip 118 which mates with leadscrew groove 112. Bearing 114 is held in place by means of sleeve bearing retention screws 98, 100 and 102 which are threadably mounted on boom 26 and which converge on bearing groove 116 in sleeve bearing 114. When leadscrew 106 is mounted inside boom 26, it is free to rotate about its axis 88.

Rearward boom end 30 is equipped with axial slots 122 and 124. Rearward boom end 30 is further equipped with a circumferential groove 120.

Referring next to FIG. 3, balls 132, 134 and 136 are shown mounted inside slot 21 of forward catheter support 20. Forward catheter support 20 is equipped with a transverse bore 126. Retainer pin 130 is mounted inside bore 128 of forward catheter support 20.

Figure 4:
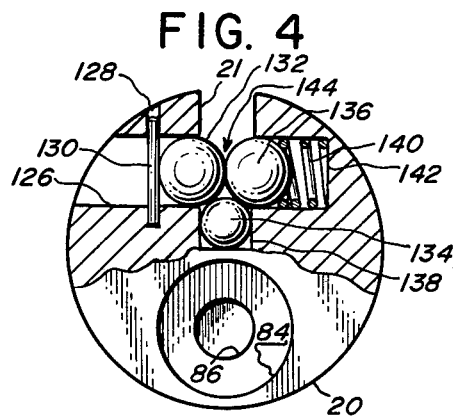
FIG. 4 is a partially cut away side view of the forward catheter support shown in FIG. 1.

As shown in FIG. 4, balls 132, 134 and 136 converge to form catheter retaining space 144. Ball 134 is mounted inside bore 138 of forward catheter support 20. In practice, a catheter (not shown) is inserted in slot 21 and is forced into catheter retaining space 144. Thus, balls 132, 134 and 136 each contact the catheter and serve to trap the catheter within the catheter retaining space 144. Ball 136 is forced towards ball 132 and ball 134 by resilient member 140 mounted between ball 136 and transverse bore base 142. Retainer pin 130 serves to prevent ball 132 from being forced out of transverse bore 126. Balls 132, 134 and 136 are capable of rotating when a catheter is pulled through catheter retaining space 144. The restraining force opposing motion of a catheter through retaining space 144 by balls 132, 134 and 136 is controlled by the tension in resilient member 140. In practice balls 132, 134 and 136 act as a controlled restraint against catheter motion through retaining space 144.

Figure 5:
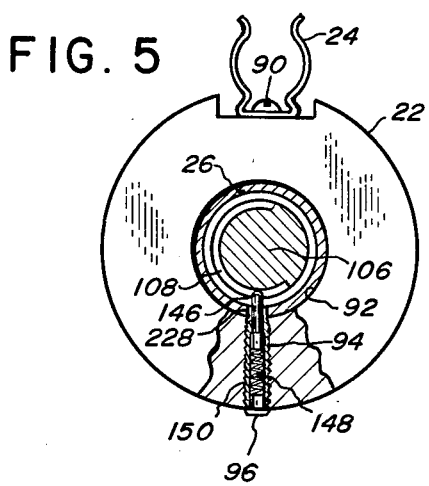
FIG. 5 is an end elevation view taken along lines 5—5 of FIG. 8 and showing portions thereof broken away for clarity.

Referring next to FIG. 5, the interaction of plunger 146 of leadscrew follower 96 with threads 108 of leadscrew 106 is shown. Plunger 146 is forced towards leadscrew 106 by resilient member 148 mounted inside body 150 of leadscrew follower 96. As shown, body 150 projects inside bore 92 and inside slot 228 of boom 26. Leadscrew follower 96 is threadably mounted in rearward catheter support 22.

Figure 6:
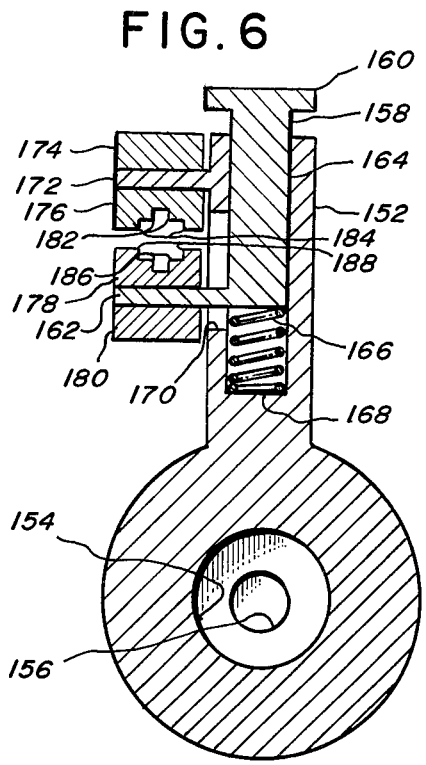
FIG. 6 shows in side cross section an alternative structure for the forward catheter support shown in FIG. 3.

Referring next to FIG. 6, a forward catheter support 152 is shown which is an alternative design to that shown in FIG. 4. Forward support 152 includes a forward support plunger 158 having a handle 160 and slidably mounted inside a bore 164. Forward support 152 has a movable jaw 162 attached thereto. Resilient member 166 provides tension between plunger bore base 168 and forward support plunger 158, thus forcing movable jaw 162 towards fixed jaw 172. As plunger 158 slides within plunger bore 164, movable jaw 162 moves along jaw slot 170. Jaw coverings 174 and 176 are preferably composed of the same length of tubular material slipped over fixed jaw 172. Jaw coverings 174 and 176 are firmly attached to fixed jaw 172 and are preferably composed of elastomeric material. Jaw covering 176 has upper back ridges 182 and upper front ridges 184 cut therein. Jaw coverings 178 and 180 are preferably composed of a single length of tubular material slipped over movable jaw 162. Jaw coverings 178 and 180 are preferably composed of elastomeric material and are fixed to movable jaw 162. Jaw covering 178 includes lower back ridges 186 and lower front ridges 188 cut therein.

In operation, handle 160 of plunger 158 is depressed manually and a catheter (not shown) is inserted between jaw covering 178 and jaw covering 176. For small catheters, line contacts will be stablished between the catheter and the jaw coverings 176 and 178 by ridges 182 and ridges 186. For larger catheters, line contacts will be established between the catheter and jaw coverings 176 and 178 by ridges 184 and ridges 188. Ridges cut in the jaw coverings of the forward catheter support establish controlled amounts of friction between the catheter and the jaw covering. Tension supplied by resilient member 166 controls the amount of resistance to catheter motion supplied by the jaw coverings 176 and 178. Boom bore 154 and leadscrew bore 156 perform functions analogous to boom bore 84 and leadscrew bore 86 shown in FIG. 4.

Figure 7:
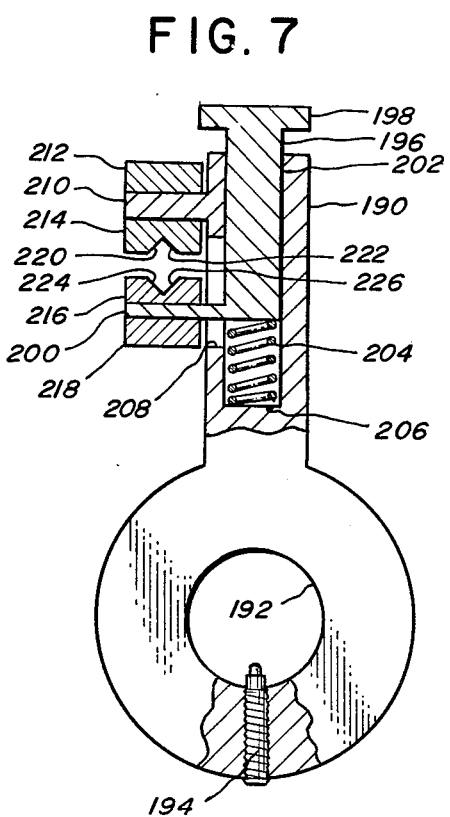
FIG. 7 shows a partially cut away side view of an alternative structure for use as a rearward catheter support in conjunction with the forward catheter support shown in FIG. 6.

Referring now to FIG. 7, rearward catheter support 190 is shown which may be used in conjunction with forward catheter support 152 shown in FIG. 6. Support 190 performs a function analogous to that performed by rearward catheter support 22 shown in FIG. 5. Plunger 196 has a handle 198 and is slidably mounted in plunger bore 202 of rearward catheter support 190. Plunger 196 has movable jaw 200 attached. Plunger 196 is forced upwards by resilient member 204 mounted inside bore 202 and bearing against bore base 206. As plunger 196 slides along bore 202, movable jaw 200 travels inside slot 208. Fixed jaw 210 is firmly attached to rearward catheter support 190 and has jaw coverings 212 and 214 attached. Jaw coverings 212 and 214 are preferably composed of a single length of tubular material slipped onto fixed jaw 210. Similarly, jaw coverings 216 and 218 preferably are composed of a single length of tubing slipped onto jaw 200. Jaw covering 214 has upper surfaces 220 and 222 cut therein. Jaw covering 216 has lower surfaces 224 and 226 cut therein. In practice, handle 198 is depressed to allow a catheter (not shown) to be inserted between jaw covering 214 and jaw covering 216. The catheter is contacted by surfaces 220, 222, 224 and 226. Jaw coverings 214 and 216 are forced together by tension in resilient member 204. When the catheter is placed between jaw coverings 214 and 216, large frictional forces exist on the surfaces 220, 222, 224 and 226 which prevent catheter motion. Rearward catheter support 190 is further equipped with bore 192 and leadscrew follower 194 which function analogously to bore 92 and leadscrew follower 96 shown in FIG. 5. In operation, a catheter is mounted in rearward catheter support 190 and also is mounted in forward catheter support 152 shown in FIG. 6. As rearward catheter support 190 is moved away from forward catheter support 152, the catheter is held firmly by rearward catheter support 190 and is allowed to slip with a controlled amount of friction through forward catheter support 152. This results in the catheter being tensioned between support 152 and support 190 thus preventing the catheter from drooping or kinking.

Figure 8:
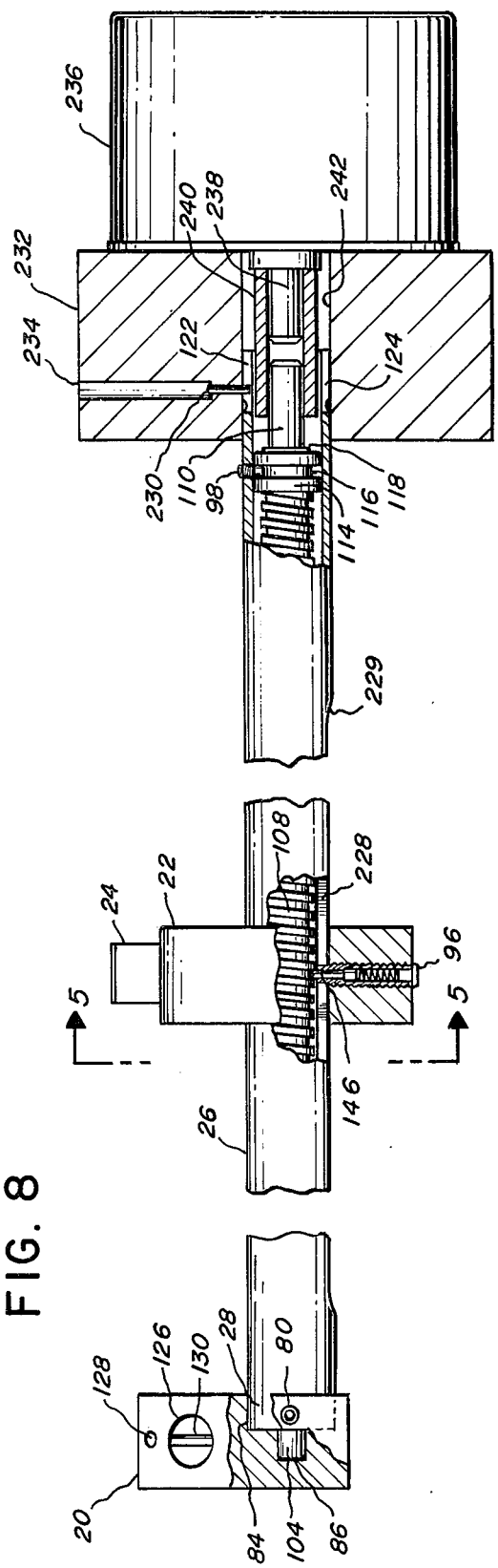
FIG. 8 shows a partially cut away side view of the structures of the invention attached to the boom.

Referring now to FIG. 8, leadscrew follower 96 is shown as riding within boom access slot 228. Boom 26 is removably mounted inside transverse bore 242 of motor mounting block 232. In a completed assembly, motor mounting block 232 is mounted inside drive box 32 shown in FIG. 1. Boom 26 is prevented from rotating in bore 242 by locating pin 230 which fits inside slot 122. Locating pin 230 is securely mounted inside bore 234 of motor mounting block 232. Leadscrew rearward end 110 is coupled to drive motor shaft 238 by means of coupling member 240. Drive motor 236 is securely mounted to motor mounting block 232. Boom 26 is capable of being pulled out of bore 242 so that boom 26 and all components attached thereto may be sterilized. Boom 26 may also be removed from bore 242, rotated 180° and reinserted inside bore 242 so that locating pin 230 fits within slot 124. Normally, boom 26 is rotated so that locating pin 230 fits within slot 124 when vertical catheter pulls are to be done. Coupling member 240 preferably comprises a length of silicone tubing firmly attached to drive motor shaft 238. Coupling member 240 preferably has an inner diameter less than the outside diameter of leadscrew rearward end 110 so that leadscrew rearward end 110 is tightly grasped by coupling member 240 when inserted inside coupling member 240. Coupling member 240 acts to transfer rotational motion between motor shaft 238 and leadscrew rearward end 110. As leadscrew rearward end 110 is rotated, rearward catheter support 22 is propelled towards motor mounting block 232 since plunger 146 follows threads 108. When leadscrew follower 96 reaches slot end 229, motion of rearward support 22 ceases and plunger 146 is forced to move in and out of threads 108 as leadscrew end 110 rotates. Also, rearward catheter support 22 may be manually slid along boom 26 and plunger 146 will move in and out of threads 108.

Figure 9:
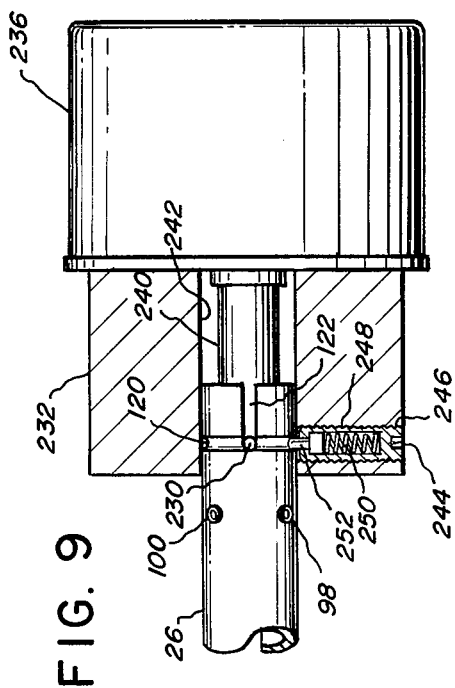
FIG. 9 shows a partially cut away top view of the invention showing the structure connecting the boom and the motor.

Now referring to FIG. 9, action by boom retainer 224 to releasably retain boom 26 inside bore 242 is shown. Boom retainer 244 includes plunger 252 and resilient means 250 mounted inside retainer case 248. Boom retainer 244 is threadably mounted inside bore 246 of motor mounting block 232. Resilient means 250 forces plunger 252 towards groove 150 in boom 26. In use, boom 26 is inserted in bore 242 and releasably retained in place by plunger 252 mounting inside groove 120.

Figure 10:
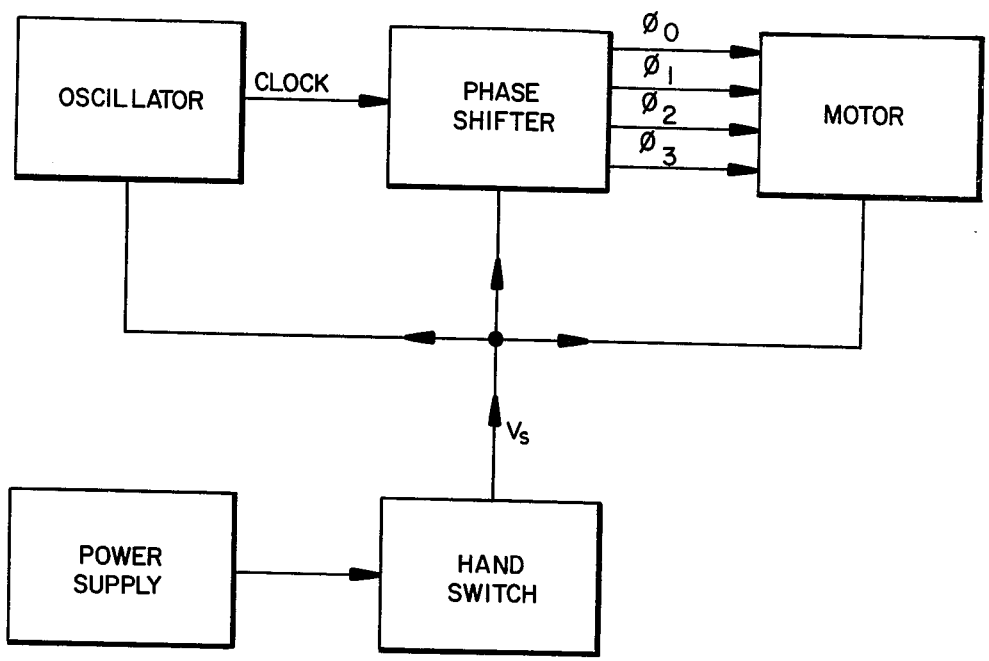
FIG. 10 is a block diagram of the electrical circuitry used in the instant invention.

Referring now to FIG. 10, a block diagram of the electrical circuitry controlling the drive motor is shown. Power to the oscillator, phase shifter, and motor is gated by the hand switch from the power supply. The hand switch is preferably a push button which gates power to the oscillator, phase shifter and motor when depressed. When the push button is depressed, the oscillator generates a clock signal which is applied to the phase shifter. The phase shifter is controlled by the clock signal and generates four output signals $\phi_0$, $\phi_1$, $\phi_2$ and $\phi_3$. The motor in this particular embodiment of the invention is a four winding stepper motor which will produce rotations when the signals $\phi_0$, $\phi_1$, $\phi_2$ and $\phi_3$ are applied to its windings. When power from the power supply is not gated through the hand switch to the oscillator, phase shifter, and motor, no rotations are produced by the motor.

Figure 11:
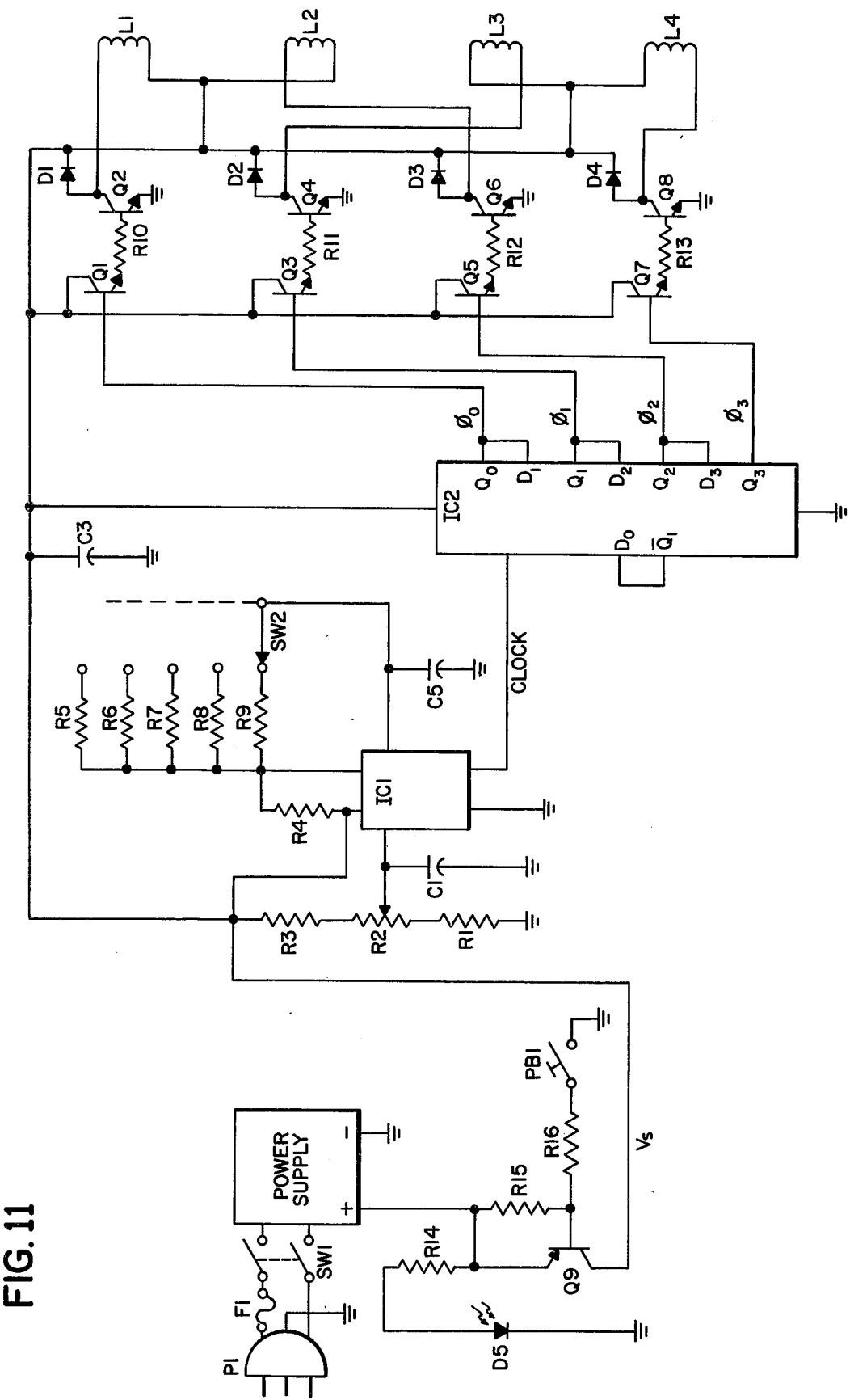
FIG. 11 is an electrical schematic diagram of the circuitry shown in FIG. 10.

Referring next to FIG. 11, a schematic diagram of the electrical circuit used in this embodiment of the invention to control the revolutions produced by the motor is shown. The hand switch section of FIG. 10 is shown as push button PB1. Push button PB1 corresponds to motor control switch 64 shown in FIG. 1. The power supply section of FIG. 10 is shown here as a power supply which converts AC obtained through plug P1, fuse F1 and switch SW1 into DC controlled by transistor Q9 and resistors R15 and R16. Plug P1, fuse F1 and switch SW1 correspond to power plug 78, fuse 74 and power switch 70, respectively, as shown in FIG. 1. When plug P1 is supplied with AC and switch SW1 is closed, current passes through resistor R14 causing light emitting diode D5 to light. Light emitting diode D5 corresponds to pilot light 72 shown in FIG. 1. Closing push button PB1 allows current to flow from the emitter to the collector of transistor Q9 thus establishing a supply voltage $V_S$. Capacitor C3 is connected between $V_S$ and ground.

The oscillator section of FIG. 10 is shown in FIG. 11 as a network of resistors and capacitors attached to integrated circuit IC1, preferably an LM555CN multipurpose timer integrated circuit. In operation, the frequency of the clock signal generated by IC1 is varied by moving switch SW2 to connect resistor R5, R6, R7, R8 or R9 into the oscillator timing circuit consisting of R4 and C5. Switch SW2 corresponds to speed control knob 36 shown in FIG. 1. Potentiometer R2 is used to fine tune the clock frequency. In practice, the rotational speed produced by the motor is calibrated by adjusting R2. Resistors R3 and R1 combine with R2 to form a voltage divider which determines the sensitivity of the clock frequency to changes in R2. Capacitor C1 is connected to the wiper of R2.

The phase shifter section of FIG. 10 is shown in FIG. 11 as integrated circuit IC2, preferably an MM74C175N integrated circuit containing four D flip-flops. The flip-flop inputs for the four flip-flops are labeled $D_0$, $D_1$, $D_2$ and $D_3$. The corresponding flip-flop outputs are labeled $Q_0$, $Q_1$, $Q_2$ and $Q_3$. An inverted output of $Q_1$ is shown as $\overline{Q_1}$. As shown in the drawing, the four output signals $\phi_0$, $\phi_1$, $\phi_2$ and $\phi_3$ are produced by the flip-flop outputs $Q_0$, $Q_1$, $Q_2$ and $Q_3$, respectively. By connecting $D_1$ to $Q_0$, $D_2$ to $Q_1$ and $D_3$ to $Q_2$, a non-recirculating shift register is formed. Connecing $D_0$ to $\overline{Q_1}$ causes $\phi_0$ to have a frequency one-fourth that of the clock and causes $\phi_1$ to also have a frequency one-fourth that of the clock but to lag $\phi_0$ by one clock period. Similarly, $\phi_2$ has the waveshape of $\phi_1$ delayed by one clock period. The output signal $\phi_3$ has the waveshape of $\phi_2$ delayed by one clock period.

Each of the four output signals are applied to a power amplifying transistor pair which is connected to a winding of the stepper motor. $\phi_0$ is applied to the base of transistor Q1 which controls the base current of transistor Q2 through resistor R10. When signal $\phi_0$ is applied, Q2 allows current to flow through stepper motor winding L1. When transistor Q2 turns "off", suppression diode D1 dampens the switching transient resulting from the inductance in winding L1. Similarly, the excitation of stepper motor winding L3 is controlled by output signal $\phi_1$ acting through transistor Q3, resistor R11, and transistor Q4. Suppression diode D2 acts to dampen switching transients caused in winding L3. $\phi_2$ acts through transistor Q5, resistor R12 and transistor Q6 to control excitation of stepper motor winding L2, and suppression diode D3 dampens switching transients caused in winding L2. In a similar way, power is applied to stepper motor winding L4 by signal $\phi_3$ acting through transistor Q7, resistor R13, and transistor Q8. Again, suppression diode D4 suppresses switching transients induced in winding L4. The sequence in which the stepper motor windings are excited is, of course, determined by the physical construction of the stepper motor. The stepper motor is denoted by the numeral 236 in FIG. 8. Windings L1, L2, L3 and L4 are supplied with current in such a way that smooth, one directional rotation is produced by the stepper motor.

Figure 12:
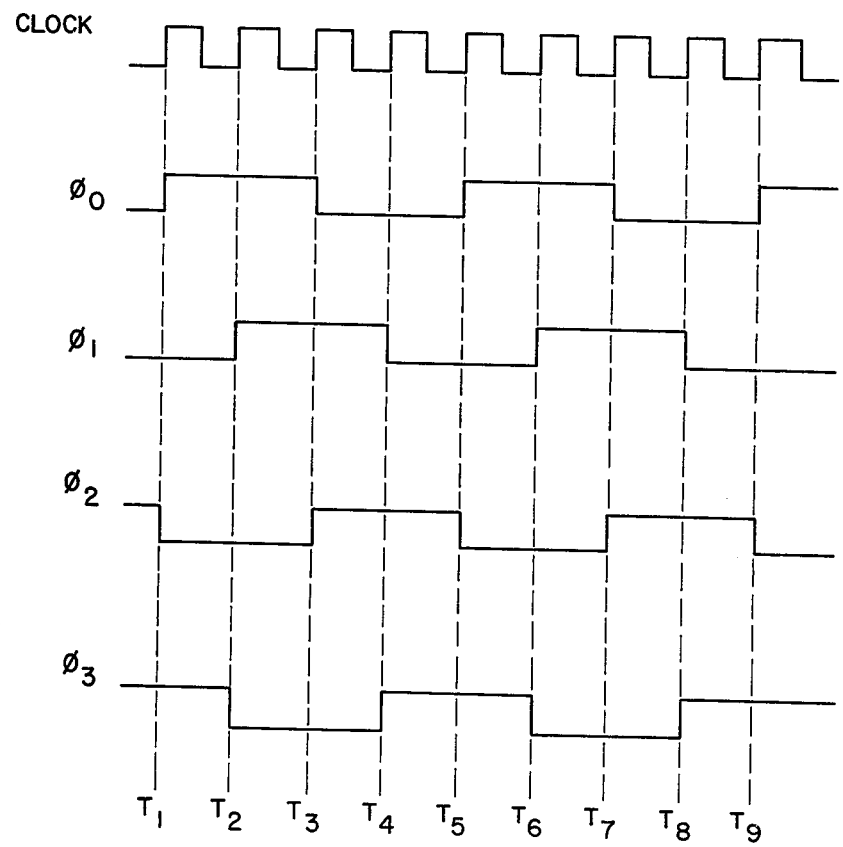
FIG. 12 is a timing diagram showing the time relationship of electrical signals generated by the circuitry of FIG. 10.

Lastly, referring to FIG. 12, voltage versus time wave shapes are shown for the clock signal and the output signals $\phi_0$, $\phi_1$, $\phi_2$ and $\phi_3$. One clock period is shown as the time duration between time $T_1$ and time $T_2$. A period of signal $\phi_0$ is shown between time $T_1$ and time $T_5$, a time duration four times longer than the period of the clock signal. Signal $\phi_1$ is a copy of $\phi_0$ delayed by one clock period. Signal $\phi_2$ is a copy of $\phi_1$ delayed by one clock period. Signal $\phi_3$ is a copy of $\phi_2$ delayed by one clock period. Thus the phase shifter of FIG. 10 generates four output signals, each having the same wave shape but each being separated in time from the other.

From the foregoing, it will be seen that this invention is one well adapted to obtain all the ends and objects herein set forth, together with other advantages which are obvious and which are inherent to the structure.

It will be understood that certain features and sub-combinations are of utility and may be employed without reference to other features and sub-combinations. This is contemplated by, and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A urethral catheter puller comprising:
   a boom;
   a forward catheter support rigidly attached to said boom and having means thereon for slidably supporting a urethral catheter;
   a rearward catheter support mounted on said boom rearwardly of said forward catheter support with respect to the point of exit of a uretheral catheter from a patient's body and having means thereon for firm attachment to a urethral catheter;
   drive means for moving said rearward catheter support along the length of said boom at a controlled rate; and
   positioning means to allow said boom to assume a plurality of angular orientations and to allow said forward catheter support to be placed in close proximity to the point of exit of a urethral catheter from a body, wherein said boom is mounted on said positioning means.

2. A urethral catheter puller comprising:
   a boom having a forward end and a rearward end;
   a forward catheter support rigidly attached to said boom adjacent said forward end and having means thereon for slidably supporting a urethral catheter;
   a rearward catheter support slidably mounted on said boom rearwardly of said forward catheter support and having means thereon for attachment to a urethral catheter;
   drive means for slidably moving said rearward catheter support along the length of said boom at a controlled rate; and
   mounting means mounted to said rearward catheter support for mounting said rearward catheter support on said boom and allowing said rearward catheter support to be manually slid along the length of said boom independently of the operation of said drive means.

3. The urethral catheter puller of claim 2 wherein said drive means comprises:
   a leadscrew operatively connected to said mounting means, wherein said mounting means includes follower means operatively connecting said leadscrew with said rearward catheter support so that said rearward catheter support is slidably moved along said boom as said leadscrew is rotated;
   a motor; and
   means connecting said motor to said leadscrew so that said leadscrew is caused to rotate by said motor.

4. The urethral catheter puller of claim 3 wherein said follower means comprises:
   a plunger mounted in said rearward catheter support and positioned to fit within the threads of said leadscrew;
   a resilient member mounted in said rearward catheter support and positioned to force said plunger towards said leadscrew to cause said plunger to follow said threads thus causing said rearward support to slidably move along the length of said boom as said leadscrew is rotated, and also to allow said rearward support to be manually repositioned along the length of said boom without rotating said leadscrew by allowing said plunger to move in and out of said threads.

5. The urethral catheter puller of claim 3 wherein said means connecting said leadscrew to said motor comprises:
   a coupling member mounted on and between said leadscrew and said motor and releasably grasping said leadscrew thus allowing said boom to be removed from said motor; and
   means including a locating pin to prevent said boom from rotating with respect to said motor.

6. The urethral catheter puller of claim 1 or claim 2 wherein said means for slidably supporting a urethral catheter on said forward catheter support comprises:
   a plurality of rotatable balls mounted on said forward catheter support so as to releasably confine a catheter.

7. The urethral catheter puller of claim 1 or claim 2 wherein said means for slidably supporting a uretheral catheter on said forward catheter support comprises:
   opposing jaws mounted on said forward catheter support to clamp to a catheter and having a plurality of ridges mounted on said jaws in opposing relation to contact with said catheter.

8. The urethral catheter puller of claim 1 or claim 2 wherein said drive means comprises:
   a stepper motor; and
   control circuitry for said motor comprising a variable frequency oscillator, and a non-recirculating shift register which is supplied with an electrical signal from said oscillator and which is connected to said stepper motor to control the speed of said motor and thereby withdraw said catheter at a controlled rate.

* * * * *